US012453541B2

(12) United States Patent
Lee et al.

(10) Patent No.: US 12,453,541 B2
(45) Date of Patent: Oct. 28, 2025

(54) SURGICAL TOOL FIXING DEVICE FOR SURGICAL ROBOT

(71) Applicant: CUREXO, INC., Seoul (KR)

(72) Inventors: Chang Hun Lee, Seoul (KR); Kwan Ju Lee, Seoul (KR)

(73) Assignee: CUREXO, INC., Seoul (KR)

( * ) Notice: Subject to any disclaimer, the term of this patent is extended or adjusted under 35 U.S.C. 154(b) by 0 days.

(21) Appl. No.: 18/877,688

(22) PCT Filed: May 9, 2023

(86) PCT No.: PCT/KR2023/006254
§ 371 (c)(1),
(2) Date: Dec. 20, 2024

(87) PCT Pub. No.: WO2023/249247
PCT Pub. Date: Dec. 28, 2023

(65) Prior Publication Data

US 2025/0169805 A1 May 29, 2025

(30) Foreign Application Priority Data

Jun. 21, 2022 (KR) ........................ 10-2022-0075465

(51) Int. Cl.
*A61B 17/00* (2006.01)
*A61B 34/30* (2016.01)

(52) U.S. Cl.
CPC .............. *A61B 17/00* (2013.01); *A61B 34/30* (2016.02); *A61B 2017/00477* (2013.01)

(58) Field of Classification Search
CPC .......... A61B 2017/00477; A61B 34/30; A61B 17/00
See application file for complete search history.

(56) References Cited

U.S. PATENT DOCUMENTS

| | | | | |
|---|---|---|---|---|
| 2011/0245833 | A1* | 10/2011 | Anderson | A61B 17/1628 606/80 |
| 2018/0353248 | A1 | 12/2018 | Bowling et al. | |
| 2020/0246025 | A1 | 8/2020 | Akhlaghpour et al. | |
| 2022/0110616 | A1 | 4/2022 | Rubrecht et al. | |
| 2023/0047595 | A1* | 2/2023 | Elsawah | A61B 90/39 |

FOREIGN PATENT DOCUMENTS

| | | | |
|---|---|---|---|
| JP | 6385275 | B2 | 9/2018 |
| JP | 2020018844 | A | 2/2020 |
| KR | 20080100212 | A | 11/2008 |
| KR | 10-2020-0000440 | A | 1/2020 |
| KR | 10-2307866 | B1 | 10/2021 |
| KR | 10-2359592 | B1 | 2/2022 |

* cited by examiner

*Primary Examiner* — Daniel Jeremy Leeds
(74) *Attorney, Agent, or Firm* — Bridgeway IP Law Group, PLLC; Jihun Kim

(57) ABSTRACT

An embodiment relates to a surgical tool fixing device for a surgical robot, and more particularly to a surgical tool fixing device for a surgical robot, which stably fixes and supports a shaft support sleeve for a surgical tool having a shaft like a drill, so that related components can be prevented from deformation and improved in durability, and the surgical tool can be conveniently and stably separated and mounted without difficulty.

2 Claims, 9 Drawing Sheets

SURGICAL TOOL FIXING DEVICE FOR SURGICAL ROBOT

TECHNICAL FIELD

The disclosure relates to a surgical tool fixing device for a surgical robot, and more particularly to a surgical tool fixing device for a surgical robot, which stably fixes and supports a shaft support sleeve for a surgical tool having a shaft like a drill, so that related components can be prevented from deformation and improved in durability, and the surgical tool can be conveniently and stably separated and mounted without difficulty.

BACKGROUND ART

In general, surgical treatment for joint diseases includes arthroscopic surgery, chondrocyte transplantation, etc. and includes artificial joint surgery for severe conditions. As representative artificial joint surgery, there are manual artificial joint surgery manually performed by medical personnel, and robotic artificial joint surgery performed by a robot.

The robotic artificial joint surgery refers to a surgical procedure of placing an artificial knee joint (implant) after cutting a patella by rotating a cutter of a cutting device mounted to a distal end of a position-variable arm of the robot based on information input to a computer, and employs a cutting device including a drill or the like cutting tool (hereinafter referred to as a drill).

FIG. 1A is a perspective view showing a mounted state to describe a conventional surgical tool fixing device for an orthopedic surgical robot, and FIG. 1B is a perspective view showing a separated state to describe the conventional surgical tool fixing device for the orthopedic surgical robot.

Referring to FIGS. 1A and 1B, the conventional surgical tool fixing device A for the orthopedic surgical robot includes a sleeve 200 for supporting a drill 100 that performs a cutting operation, a chuck device 300 for holding the drill 100, a holder 400 installed with the chuck device 300 and mounted to the distal end of the position-variable arm (not shown) of the robot, an operation nut 500 for applying operating force to lock or release the drill 100 to or from the chuck device 300, and a motor (not shown) mounted to a motor joining member 600 coupled to the holder 400 so as to provide rotational force to the drill 100.

Details of the foregoing components are as follows. The drill 100 includes a head 110 formed with a cutting edge, and a shaft 120 extending from the head 110 and shaped like a rounded rod. The drill 100 performs the cutting operation as the rear end of the shaft 120 connected to the motor rotates, in which the outer circumferential surface of the shaft 120 is rotatably supported by the sleeve 200 and prevented from shaking or bending while rotating, and the head 110 protruding out of the sleeve 200 rotates to cut the bone.

The sleeve 200 includes a pipe portion 210 having a small diameter, and a fastening cap 220 formed at one end of the pipe portion 210 and fastened to the chuck device 300, and a bearing 230, a spacer 240, etc. are inserted in the sleeve 200 to rotatably support the shaft 120 of the drill 100.

The chuck device 300 is configured to perform a clamping operation or an unclamping operation by pressing or releasing the shaft 120 of the drill 100 as a chuck 320 (usually referred to as a collet with three or four jaws moving radially to hold the shaft of the drill or the like) provided in front of a chuck body 310 is closed or opened. Among the well-known chuck devices, medical chuck devices used in orthopedics, dentistry, etc. may be used as the chuck device 300.

Further, the chuck body 310 is formed with an operation-force applying portion (not shown) such as an adjusting screw portion to which the operation nut 500 is fastened, so that the chuck 320 can be closed to press and lock the shaft when the operation nut 500 rotates in a certain direction, and the chuck 320 can be opened to release the shaft when the operation nut 500 rotates in a reverse direction.

The above-described conventional surgical tool fixing device for the orthopedic surgical robot supports the drill 100 to perform the cutting operation, but has limitations causing problems as follows.

In the conventional surgical tool fixing device A for the orthopedic surgical robot, a large load acting left and right is applied to the sleeve 200 while the drill 100 moves left and right during the cutting operation. When the large load is applied left and right to the sleeve 200, the sleeve 200 is slightly deformed left and right because the sleeve 200 has a long cantilever structure and is screw-coupled to the front of the chuck body 310 with a separation distance d therebetween without any separate support means. The deformation of the sleeve 200 causes the shaft 120 of the drill 100 and related components (e.g., a bearing) to be deformed and decreased in durability, and also causes the chuck device 200 into which the shaft 120 is locked to be deformed and decreased in durability. Due to such limitations, there are disadvantages that frequent component replacement increases maintenance costs, surgery is performed unstably, there is a high risk of negligent accidents, and the downtime of surgery increases.

Further, in the conventional surgical tool fixing device A for the orthopedic surgical robot, there is a need for rotating the operating nut 500 to release or lock the shaft 120 from or to the chuck device 300 when the drill 100 is to be cleaned or replaced. However, it is very difficult for a female nurse or the like user, who has a weak grip, to rotate the operating nut 500 or tightly lock the shaft 120, thereby causing erroneous operations or negligent accidents.

DISCLOSURE

Technical Problem

The disclosure is conceived to solve the foregoing problems, and an aspect of the disclosure is to provide a surgical tool fixing device for a surgical robot, which stably fixes and supports a shaft support sleeve for a surgical tool having a shaft, so that related components can be prevented from deformation and improved in durability.

Another aspect of the disclosure is to provide a surgical tool fixing device for a surgical robot, which allows a surgical tool to be conveniently and stably separated and mounted with small force.

Technical Solution

According to an aspect of the disclosure, a surgical tool fixing device for a surgical robot includes: a sleeve configured to support a surgical tool including a shaft; a chuck device including a chuck body to which the sleeve is coupled, a chuck provided inside the chuck body and selectively holding the shaft to fix the surgical tool, and an operation-force applying portion configured to apply operating force for a clamping operation and an unclamping operation of the chuck; a holder provided with the chuck device and mounted to a distal end of a robot arm; a sleeve support formed extending from the holder and configured to seat and support the sleeve thereon not to shake; and an operation handle connected to the operation-force applying portion and configured to apply operating force.

The sleeve may include a pipe portion in which the shaft is accommodated, and a fastening cap formed in an inward end portion of the pipe portion and coupled to the chuck body.

The sleeve support may include a support protrusion extending from the holder, and a sleeve seating portion formed at an end portion of the support protrusion to come into close contact with the fastening cap.

The support protrusion may protrude forward to form an operation space within which the operation-force applying portion is placed, and the sleeve seating portion may be configured as a ring formed with a chuck hole into which the chuck body is inserted, and a contact surface shaped corresponding to and coming into close contact with an end surface of the fastening cap.

The operation handle may include a meshing portion disposed in the operation space to mesh with the operation-force applying portion, and a handle portion extending from the meshing portion.

The operation handle may include: a first handle including a first meshing portion configured to mesh with a first outer surface of the operation-force applying portion so as to be placed and mounted inside the operation space, and first handle units extending from opposite ends of the first meshing portion and formed with fastening holes; a second handle including a second meshing portion configured to mesh with a second outer surface of the operation-force applying portion, and second handle units extending from opposite ends of the second meshing portion and formed with fastening holes; and fastening members configured to be fastened to the fastening holes of the first and second handles.

According to the disclosure, the surgical tool fixing device for the surgical robot may further include a motor joining member configured to be connected to a rear portion of the chuck device and joined to a motor, wherein the holder includes a holder rod, a holder head provided in a first end of the holder rod and formed with the sleeve support and a joining hole coupled to the motor joining member, a connection plate provided in a second end of the holder rod, and an arm joining member joined to the connection plate to couple with the distal end of the robot arm.

Advantageous Effects

In a surgical tool fixing device for a surgical robot according to the disclosure, a fastening cap of a sleeve is fixed by a sleeve support without shaking and prevented from deformation even though a drill is moved left and right while applying a large load during surgery, so that a shaft of the drill, a built-in bearing of the sleeve, and a chuck device for holding the shaft can be prevented from deformation and thus improved in durability, thereby having effects on reducing maintenance costs, stably performing surgery, and lowering a risk of negligent accidents, and shortening the downtime of surgery.

Further, a surgical tool fixing device for a surgical robot according to the disclosure is convenient to be operated and used by even a user who has a relatively weak grip because an operation handle is readily rotated forward and backward with small force to perform a clamping operation and an unclamping operation when a surgical tool is to be separated or mounted.

DESCRIPTION OF DRAWINGS

FIG. 4B shows a holder and a sleeve support, FIG. 4C shows an operation handle, and FIG. 4D shows a motor joining member.

BEST MODE

Below, exemplary embodiments of the disclosure will be described in detail with reference to FIGS. 2 to 5, in which like numerals refer to like components throughout FIGS. 2 to 5.

Meanwhile, detailed descriptions about components and their operations and effects, which are easily understood by a person having ordinary knowledge in the art from general technology, in the accompanying drawings will be simplified or omitted. In addition, the disclosure is characterized in a surgical tool fixing device for a surgical robot, and thus illustration and description will be made focusing on related parts while simplifying or omitting the other parts.

Figure 2:
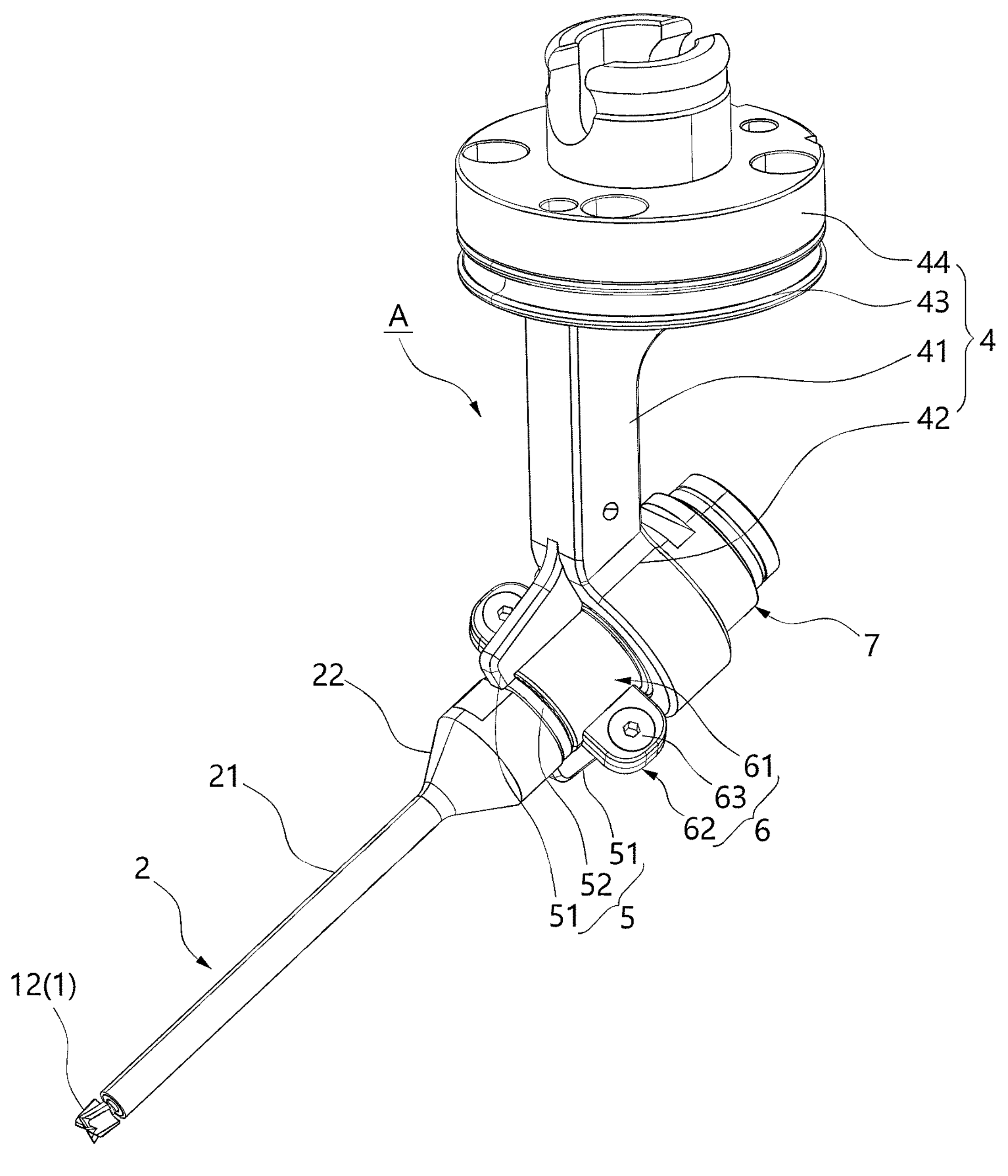
FIG. 2 is a perspective view showing a surgical tool fixing device for a surgical robot according to an embodiment of the disclosure.
Figure 3:
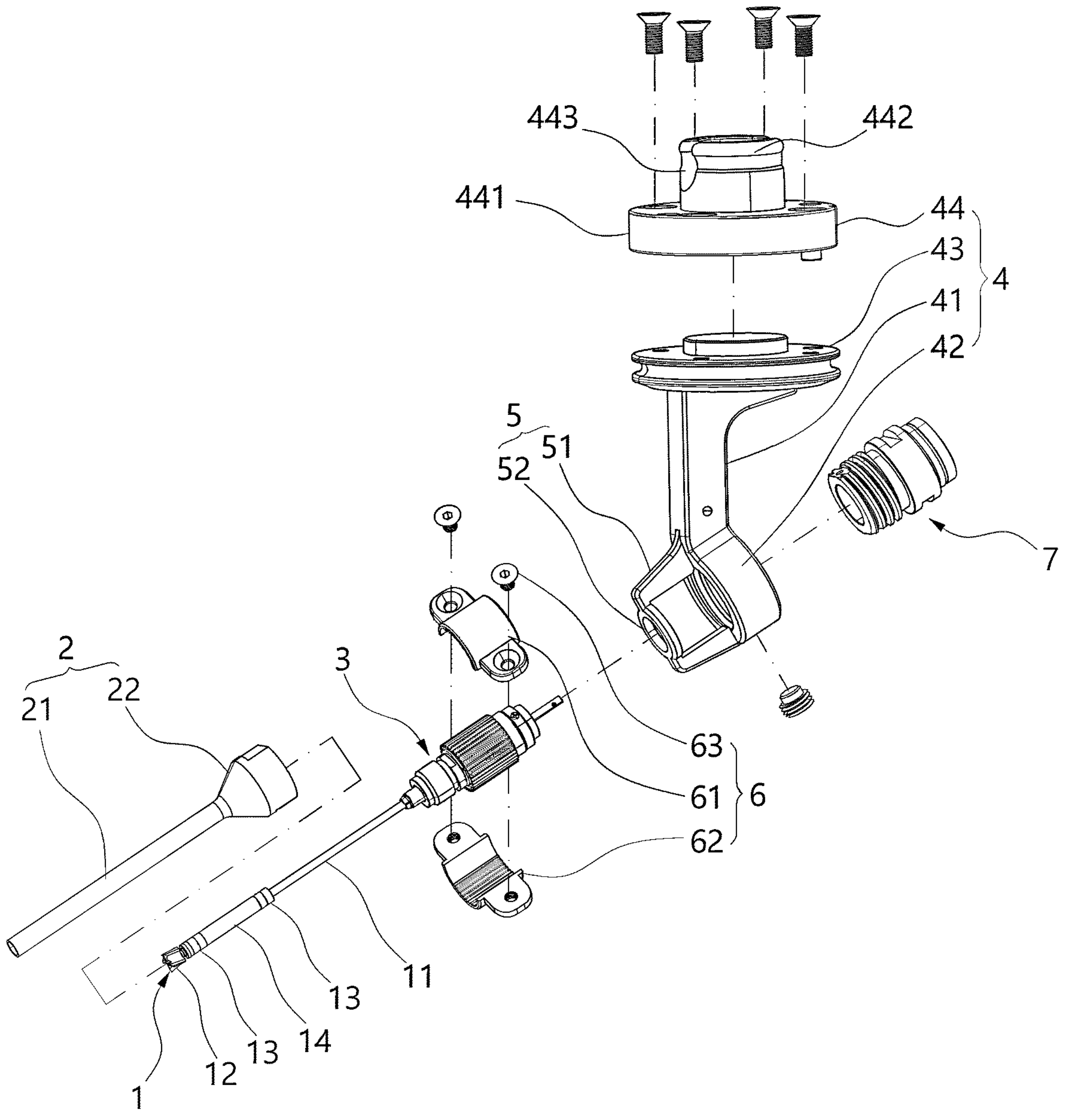
FIG. 3 is a separated perspective view showing a surgical tool fixing device for a surgical robot according to an embodiment of the disclosure.
Figure 4A:
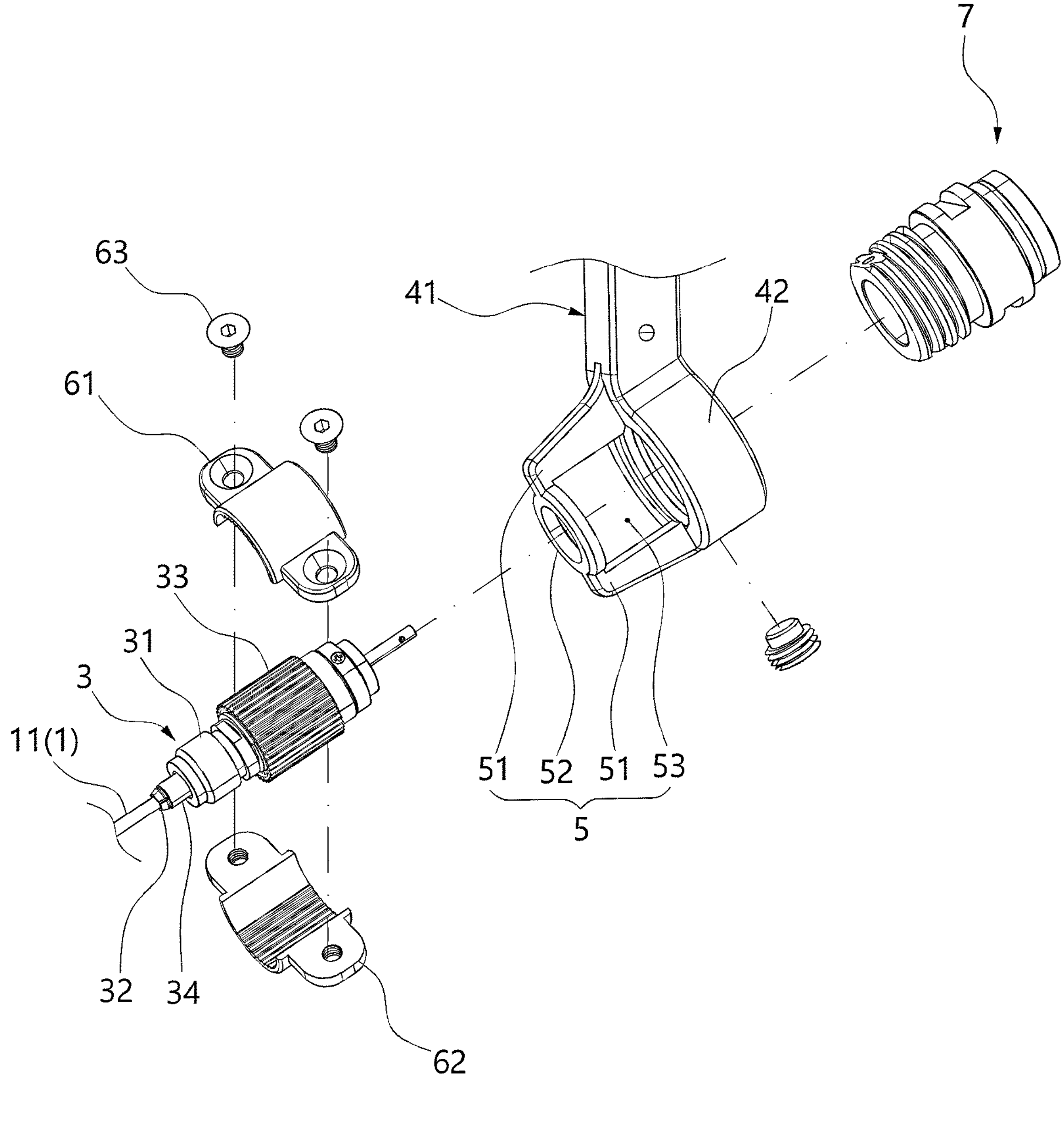
FIGS. 4A to 4D are partially enlarged views to describe a surgical tool fixing device for a surgical robot according to an embodiment of the disclosure, in which FIG. 4A divisionally shows a main component.
Figure 4B:
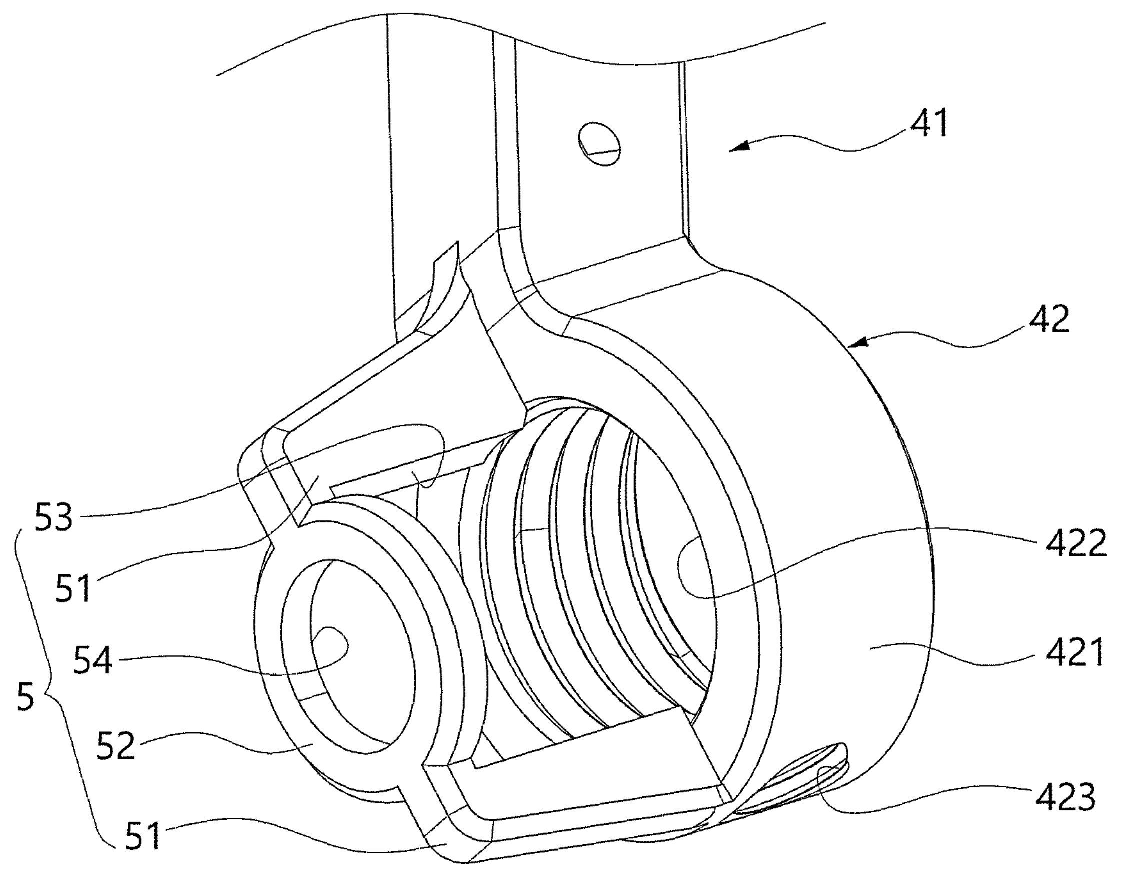
Figure 4C:
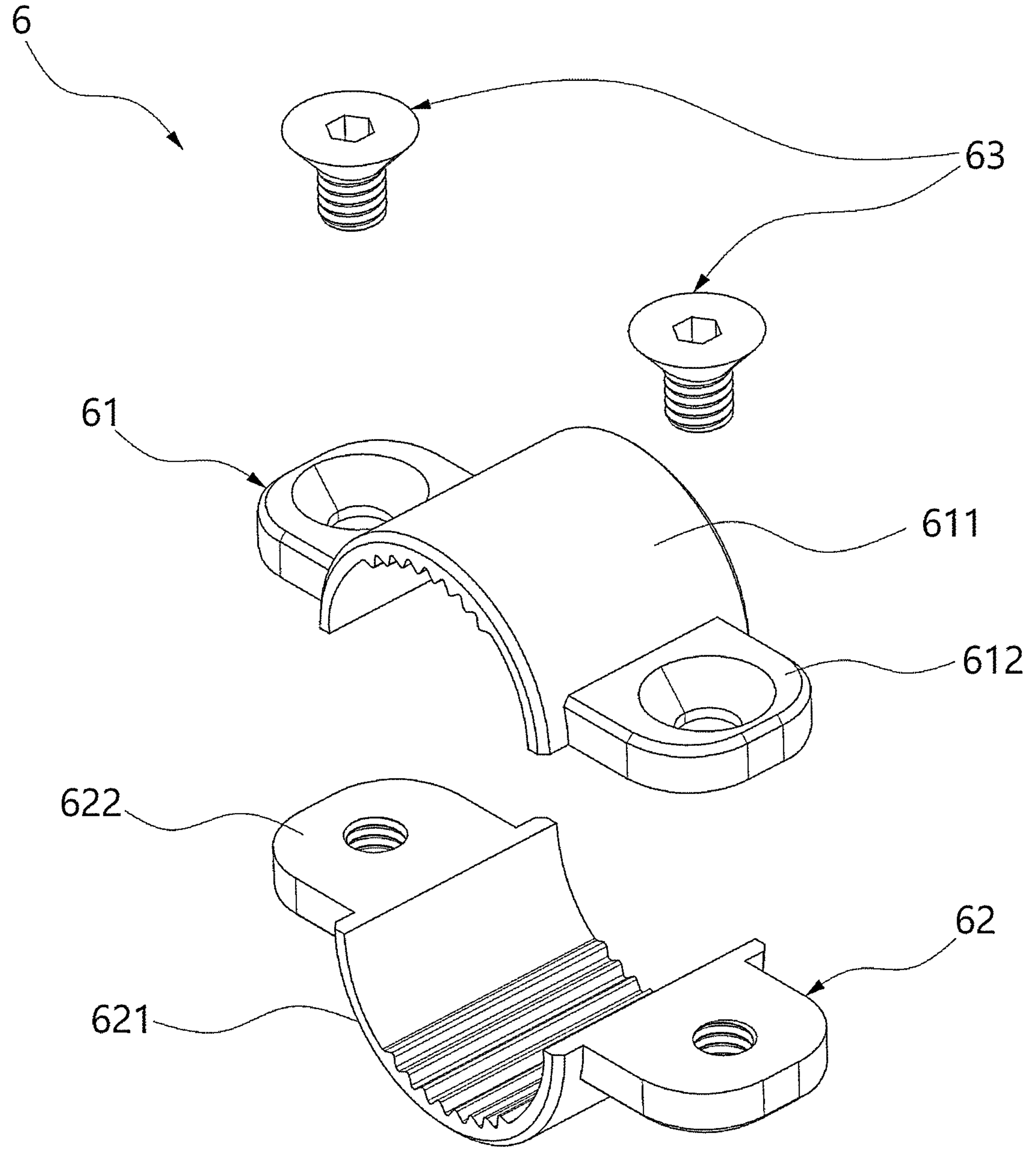
Figure 4D:
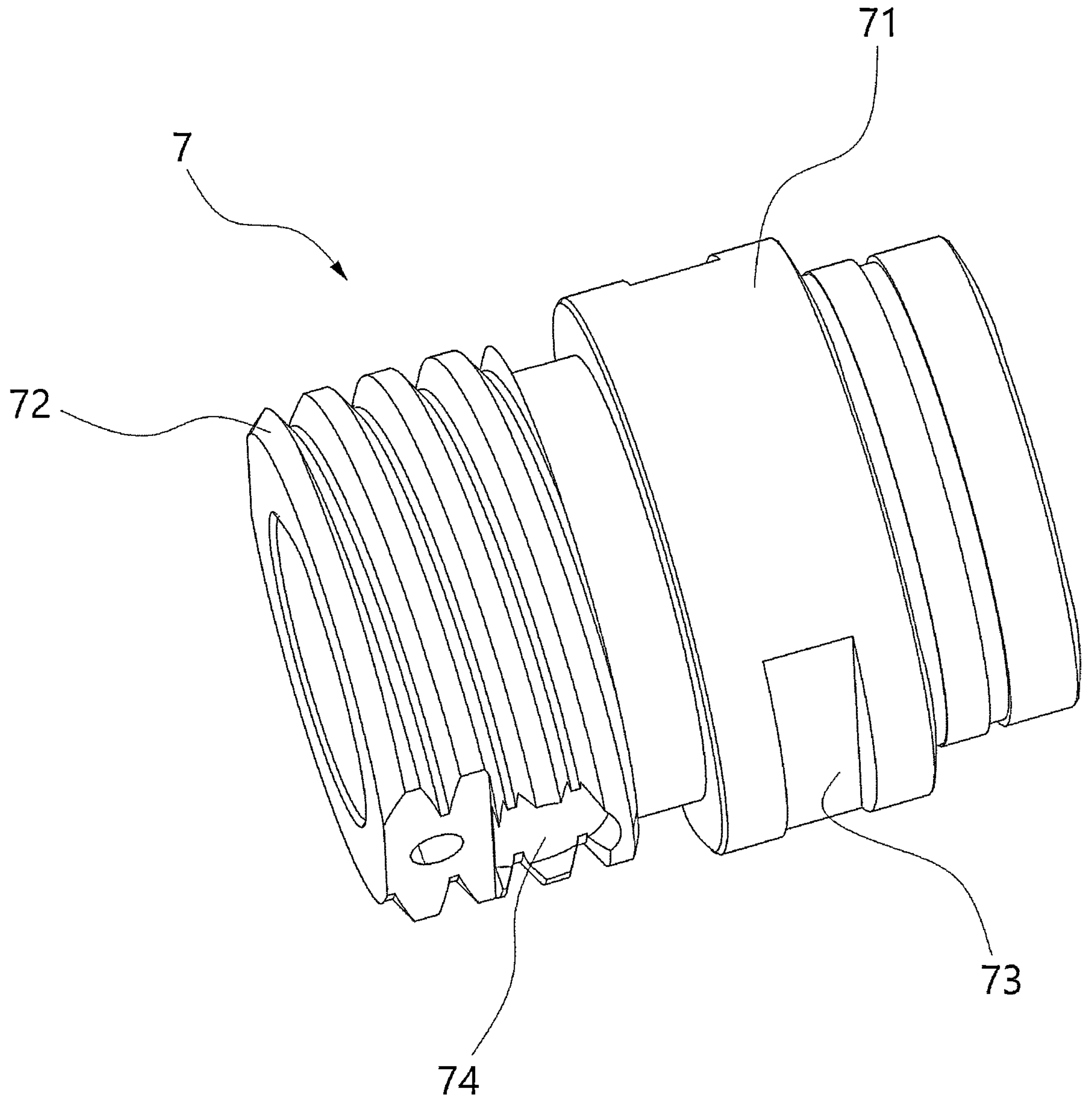
Figure 5:
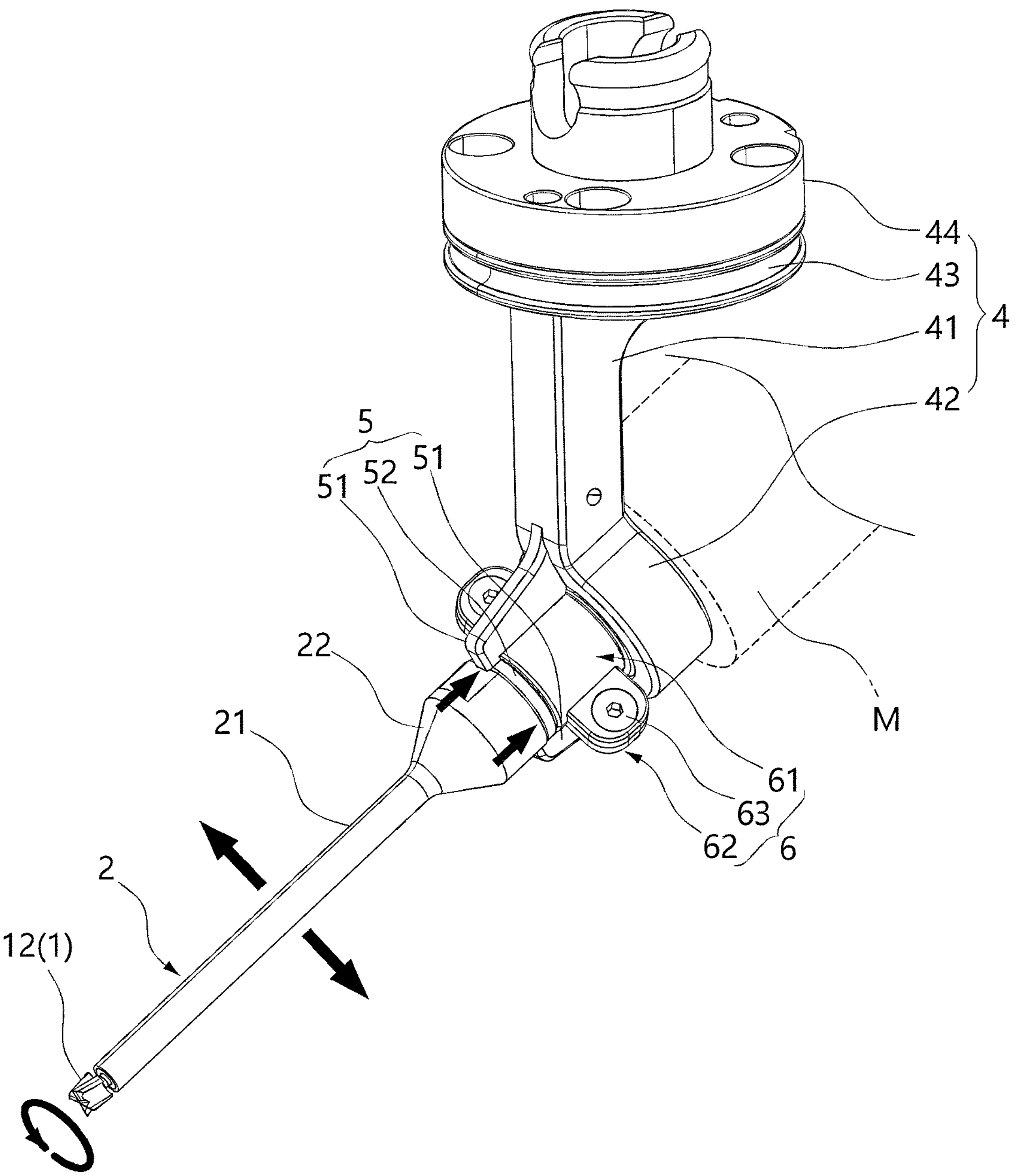
FIG. 5 is a view to describe the operations of a surgical tool fixing device for a surgical robot according to an embodiment of the disclosure.

FIG. 2 is a perspective view showing a surgical tool fixing device for a surgical robot according to an embodiment of the disclosure, FIG. 3 is a separated perspective view showing a surgical tool fixing device for a surgical robot according to an embodiment of the disclosure, FIGS. 4A to 4D are partially enlarged views to describe a surgical tool fixing device for a surgical robot according to an embodiment of the disclosure, in which FIG. 4A divisionally shows a main component, FIG. 4B shows a holder and a sleeve support, FIG. 4C shows an operation handle, and FIG. 4D shows a motor joining member, and FIG. 5 is a view to describe the operations of a surgical tool fixing device for a surgical robot according to an embodiment of the disclosure.

Referring to FIGS. 2 to 5, a surgical tool fixing device for a surgical robot according to an embodiment of the disclosure is to stably fix and support a shaft support sleeve of a surgical tool 1 having a shaft and allow the surgical tool 1 to be easily separated and mounted, and includes a sleeve 2, a chuck device 3, a holder 4, a sleeve support 5, and an operation handle 6.

The surgical tool 1 refers to a tool used in surgery, and any structure may be applied thereto as long as it has a shaft 11. According to an embodiment, description will be made based on an example of a device for fixing a drill used as a cutting tool for cutting a patella during an artificial knee joint (implant) procedure. Here, the drill used as the surgical tool 1 is fixed to the chuck device 3, and a cutting operation is performed as a motor connector (not shown) provided in the chuck device 3 is connected to a motor (not shown) and rotates. The outer circumferential surface of the shaft 11 is rotatably supported in the sleeve 2, so that the shaft 11 can rotate without shaking or bending. A head 12 protrudes outward from the sleeve 2 and rotates to perform the cutting operation for a bone.

The sleeve 2 includes a pipe portion 21 having a smaller diameter, and a fastening cap 22 formed on one end of the pipe portion 21 and fastened to a chuck body 31 (to be described later), thereby coupling with the chuck device 3. To rotatably support the shaft 11 of the drill, a bearing 13, a spacer 14, etc. are inserted in the sleeve 2.

Meanwhile, the chuck device 3 is configured to perform a clamping operation by pressing the shaft 11 of the drill or an unclamping operation by releasing the shaft 11 of the drill as a chuck 32 provided in the front of the chuck body 31 is closed or opened. Among the well-known chuck devices, medical chuck adjusting devices applied to orthopedics, dentistry, etc. may be used as the chuck device 3, and thus detailed descriptions thereof will be omitted.

For example, as shown in FIG. 4A, the chuck device 3 includes the chuck body 31 to which the sleeve 2 is coupled, the chuck 32 provided inside the chuck body 31 and selectively holding the shaft 11 to fix the surgical tool 1, and an operation-force applying portion 33 to apply operating force for the clamping operation and the unclamping operation of the chuck 32.

In addition, the chuck body 31 includes a chuck moving member 34 or the like placed inside an approximately hollow portion of a round bar-shaped body to move the chuck 32 outward and inward by the force of an internal spring when the operation-force applying portion 33 rotates forward and backward. In more detail, the chuck 32 moves backward and becomes closed to press and lock the shaft 11 when the operation-force applying portion 33 rotates in a forward direction, and the chuck 32 moves forward and becomes open to release the shaft 11 when the operation-force applying portion 33 rotates in a backward direction.

The operation-force applying portion 33 is provided as a serration gear formed on the chuck body 31 and rotated forward and backward by rotational force applied from the operation handle 6 coupled thereto.

Referring to FIGS. 3 and 4B, the holder 4 refers to a component to be mounted to the distal end of a robot arm (not shown), and includes a holder rod 41 approximately shaped like a rod, a holder head 42 formed in one end, i.e., a lower portion of the holder rod 41, a connection plate 43 formed in the other end, i.e., an upper portion of the holder rod 41, and an arm joining member 44 joined to the connection plate 43 to couple with the distal end of the robot arm.

The holder head 42 includes a ring body 421 formed with a joining hole 422 into which a motor joining member 7 (to be described later) is inserted. The ring body 421 is formed with a screw hole 423 communicating with the joining hole 422, and the sleeve support 5 described above protrudes frontward from the ring body 421.

For example, as shown in FIG. 3, the arm joining member 44 is provided as a clamp member to couple with a robot clamp member (not shown) mounted to the opposing robot arm (not shown), and the clamp member includes a clamp body 441 shaped like a disk and formed with a plurality of fastening holes, and a clamp protrusion 442 formed with a locking hole 443 put on or coupled to a clamp axis of the robot clamp member.

Meanwhile, the sleeve support 5 refers to a component formed extending from the holder 4 and supporting the sleeve 2 seated thereon not to shake, and includes a support protrusion 51 extending from the holder 4, and a sleeve seating portion 52 formed at the end of the support protrusion 51 and supporting the fastening cap 22 of the sleeve 2 to be in contact therewith.

The support protrusion 51 protrudes forward from the holder head 42 to form an operation space 53 in which the operation-force applying portion 33 is placed. According to this embodiment, two support protrusions 51 are formed at an angle of approximately 180 degrees (at an angle obtained by subtracting an angle corresponding to the thickness of the support protrusion 51 from 180 degrees) not to interfere with the forward rotation of the operation handle 6 for the clamping operation of the chuck device 3 and the backward rotation of the operation handle 6 for the unclamping operation of the chuck device 3.

The sleeve seating portion 52 is formed on the protruding end of the support protrusion 51 and configured as a ring formed with a chuck hole 54 into which the chuck body 31 is inserted. Here, the ring is structured to have a contact surface shaped corresponding to and coming into close contact with the end surface of the fastening cap 22.

The operation handle 6 refers to a component placed in the operation space 53, joined to the operation-force applying portion 33, and applying the operating force, and includes a meshing portion meshing with the operation-force applying portion 33, and a handle portion protruding from the meshing portion.

In more detail, as shown in FIGS. 4A and 4C, it is important that the operation handle 6 is configured to be assembled being placed in the operation space 53 provided inside the sleeve support 5.

To this end, the operation handle 6 is configured to have a structure separable into a first handle 61, a second handle 62, and fastening members 63 for fastening the first handle 61 and the second handle 62.

The first handle 61 is configured to mesh with one outer surface of the operation-force applying portion 33, and includes a first meshing portion 611 having an approximately semicircular body formed with a serration gear to mesh with the operation-force applying portion 33 (i.e., the serration gear), and first handle units 612 extending from the opposite ends of the first meshing portion 611 and formed with fastening holes.

The second handle 62 is configured to mesh with the other outer surface of the operation-force force applying portion 33, and includes a second meshing portion 621 having an approximately semicircular body formed with a serration gear to mesh with the operation-force applying portion 33 (i.e., the serration gear), and second handle units 622 extending from the opposite ends of the second meshing portion 621 and formed with fastening holes.

The fastening members 63 refer to members to be fastened to the fastening holes of the first and second handles 61 and 62, and include typical screws.

Meanwhile, the motor joining member 7 is configured to be connected to the rear of the chuck device 3 and joined to the motor (not shown).

As shown in FIGS. 4A and 4D, the motor joining member 7 includes a threaded portion 72 and a joining groove 73 formed on the outer circumferential surface of a round bar-shaped body 71 formed with a hollow hole into which the shaft 11 of the drill is inserted, and a screw groove 74 recessed in the threaded portion 72 to accommodate the end portion of a screw 65 inserted through the screw hole 423 of the holder head 42.

Below, the operations of the surgical tool fixing device for the surgical robot according to an embodiment of the disclosure will be described in brief.

A motor M is joined to the motor joining member 7 of the foregoing surgical tool fixing device, and the arm joining member 44 is joined to the clamping member provided in the robot arm (not shown) of the orthopedic surgical robot. The robot arm of the surgical robot, which operates based on information input to a computer, positions a surgical tool fixing device A' at a surgical site.

In this state, when the motor operates based on the information input to the computer, the surgical tool 1, e.g., the drill, fixed to the chuck device 3 rotates and cuts the set surgical site of a patella. Once such a cutting operation is performed, the procedure is performed by installing an artificial knee joint (implant) in a given order.

Figure 1A:
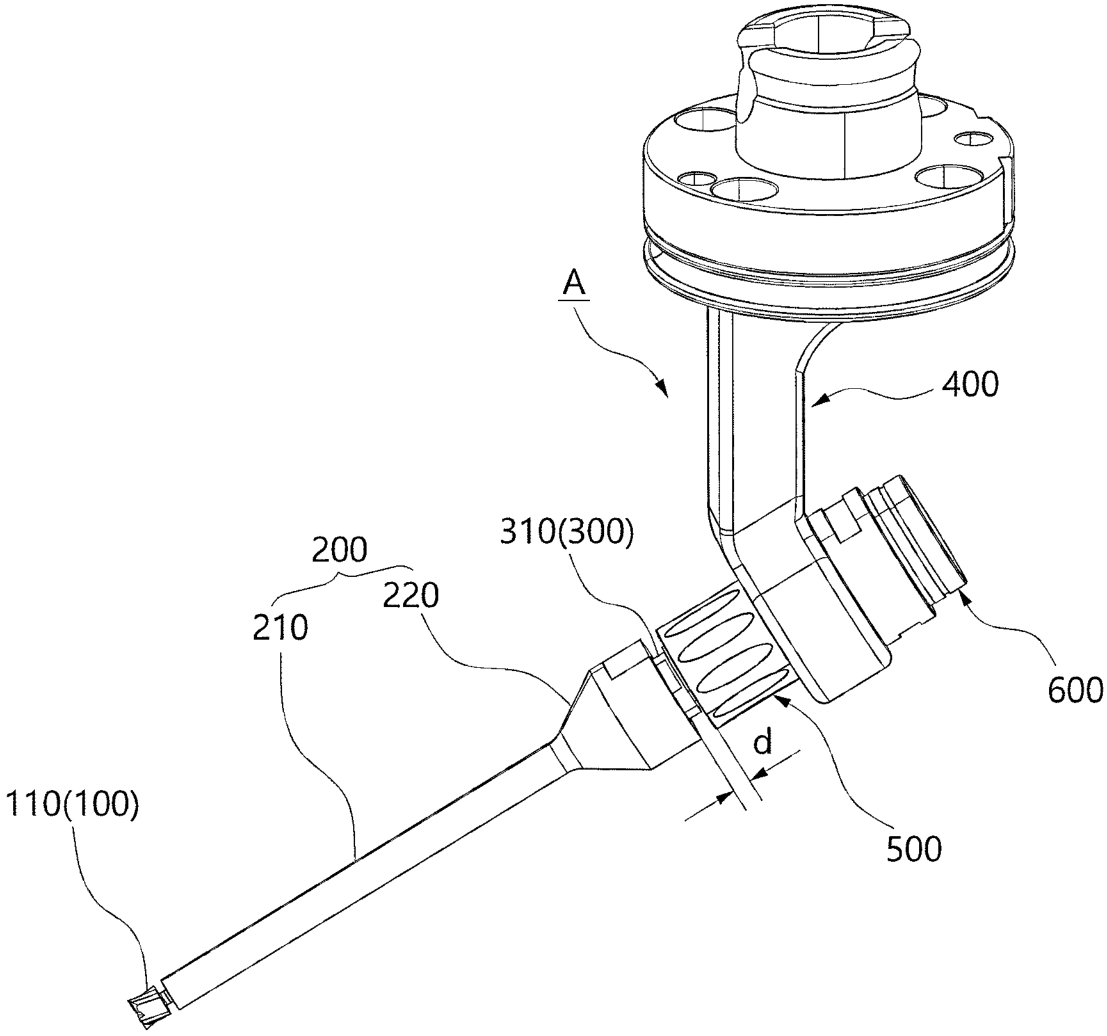
FIG. 1A is a perspective view showing a mounted state to describe a conventional surgical tool fixing device for an orthopedic surgical robot.
Figure 1B:
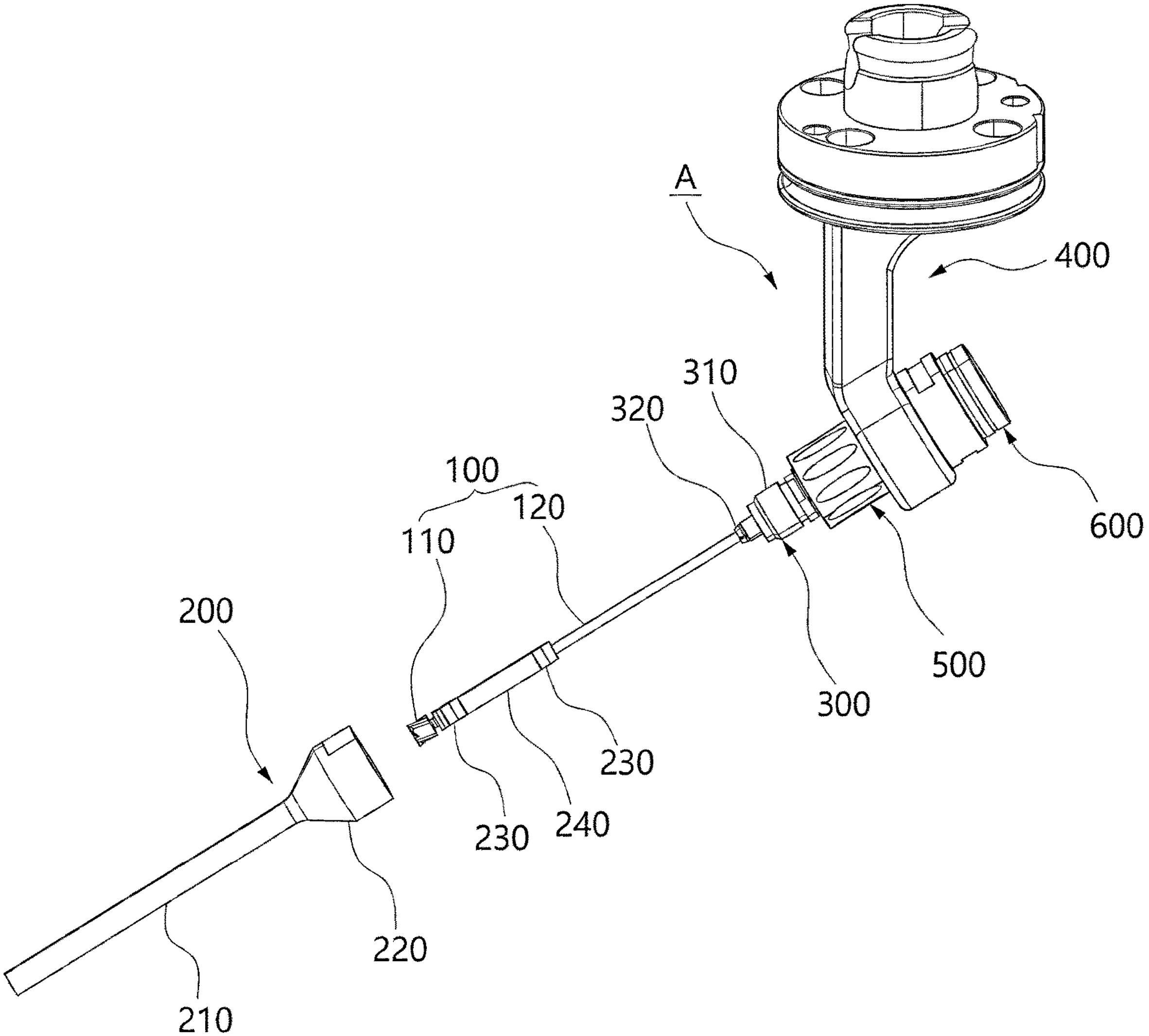
FIG. 1B is a perspective view showing a separated state to describe a conventional surgical tool fixing device for an orthopedic surgical robot.

Further, when the surgical tool 1 rotates based on the rotation of the motor, the shaft 11 is supported in the pipe portion 21 of the sleeve 2 and thus stably rotated. In this case, the fastening cap 22 of the sleeve 2 is coupled to the front of the chuck body 31, and at the same time the end surface of the fastening cap 22 is in surface-contact with the sleeve seating portion 52, thereby achieving a close contact structure not to shake. Therefore, the separation distance d (see FIG. 1A) between the conventional sleeve and the holder head is not formed, and thus the slight leftward or rightward deformation does not occur even when the surgical tool is moved with leftward or rightward force during the cutting operation.

In this way, the sleeve 2 is prevented from deformation as the fastening cap 22 is fixed to the sleeve support 5 without shaking, so that the shaft 11 of the drill and the built-in bearing or the like of the sleeve 2 can be prevented from deformation and improved in durability. In addition, the chuck device 3 to which the shaft 11 is fixed is also prevented from deformation and thus improved in durability. As a result, it is possible to reduce maintenance costs, perform surgery reliably, lower the risk of negligent accidents, and decrease the downtime of surgery.

Meanwhile, a surgical tool fixing device for a surgical robot according to the disclosure is convenient for a female nurse or the like user, who has a weak grip, to perform a clamping operation and an unclamping operation for the shaft of the surgical tool 1 without difficulties, by rotating the first and second handle units 612 and 622 protruding from the operation handle 6 180 degrees in the forward direction and 180 degrees in the backward direction when the surgical tool, i.e., the drill is to be separated or mounted for cleaning or replacement.

The terms "comprise," "configure" and/or "have" specify the presence of stated components, unless there is a clearly different meaning in the disclosure, but do not preclude the presence thereof and should be construed to further include other components. Unless otherwise defined, all terms including technical or scientific terms used herein have the same meaning as commonly understood by those skilled in the art to which the disclosure pertains. General terms that are defined in a dictionary shall be construed to have meanings that are consistent in the context of the relevant art, and will not be interpreted as having an idealistic or excessively formalistic meaning unless clearly defined in the disclosure.

Although the configurations and operations of a surgical tool fixing device for a surgical robot according to an embodiment of the disclosure have been described so far, it will be appreciated by those skilled in the art that modifications or substitutions may be made in all or part of the embodiments of the disclosure without departing from the technical spirit of the disclosure.

Accordingly, it will be understood that the scope of the disclosure falls into the appended claims and equivalents thereof.

INDUSTRIAL APPLICABILITY

Although a surgical tool fixing device for a surgical robot according to the disclosure has been described focusing on an example of fixing a surgical tool of an orthopedic surgical robot for artificial joint surgery, the surgical tool fixing device for the surgical robot is not limited to this example and may be used to stably fix and support various surgical tools with a shaft.

The invention claimed is:

1. A surgical tool fixing device for a surgical robot, comprising:

a sleeve configured to support a surgical tool comprising a shaft;

a chuck device comprising a chuck body to which the sleeve is coupled, a chuck disposed inside the chuck body and selectively holding the shaft to fix the surgical tool, and an operation-force applying portion configured to rotate forward and backward for a clamping operation and an unclamping operation of the chuck;

a holder configured to hold the chuck device and mounted to a distal end of a robot arm;

a sleeve support defined extending from the holder and configured to seat and support the sleeve thereon not to shake; and an operation handle connected to the operation-force applying portion and configured to apply operating force;

wherein the sleeve comprises a pipe portion in which the shaft is accommodated, and a fastening cap defined in an inward end portion of the pipe portion and coupled to the chuck body, the sleeve support comprises a support protrusion extending from the holder, and a sleeve seating portion defined at an end portion of the support protrusion to come into close contact with the fastening cap, the support protrusion protrudes forward to define an operation space within which the operation-force applying portion is placed, the sleeve seating portion is configured as a ring including a chuck hole into which the chuck body is inserted, and a contact surface shaped corresponding to and coming into close contact with an end surface of the fastening cap, and wherein the operation handle comprises:

a first handle placed and mounted inside the operation space, the first handle including a first meshing portion configured to mesh with a first outer surface of the operation-force applying portion, and first handle units extending from opposite ends of the first meshing portion and including first fastening holes;

a second handle including a second meshing portion configured to mesh with a second outer surface of the operation-force applying portion, and second handle units extending from opposite ends of the second meshing portion and including second fastening holes; and fastening members configured to be fastened to the first and second fastening holes of the first and second handles.

2. The surgical tool fixing device of claim 1, further comprising a motor joining member configured to be connected to a rear portion of the chuck device and joined to a motor, wherein the holder comprises a holder rod, a holder head provided in a first end of the holder rod and formed with the sleeve support and a joining hole coupled to the motor joining member, a connection plate provided in a second end of the holder rod, and an arm joining member joined to the connection plate to couple with the distal end of the robot arm.

* * * * *